(12) United States Patent
Yoo et al.

(10) Patent No.: US 8,142,631 B2
(45) Date of Patent: Mar. 27, 2012

(54) PARTICLE FOCUSING APPARATUS AND METHOD FOR FOCUSING PARTICLES BY USING THE SAME

(75) Inventors: Jung Yul Yoo, Seoul (KR); Young Won Kim, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 620 days.

(21) Appl. No.: 11/936,961

(22) Filed: Nov. 8, 2007

(65) Prior Publication Data
US 2009/0038942 A1 Feb. 12, 2009

(30) Foreign Application Priority Data
Aug. 10, 2007 (KR) .................. 10-2007-0080822

(51) Int. Cl.
G05D 7/03 (2006.01)
(52) U.S. Cl. ........................................ 204/451; 204/545
(58) Field of Classification Search .................. 204/600, 204/450–455, 545; 422/502–508
See application file for complete search history.

(56) References Cited

U.S. PATENT DOCUMENTS 5,045,172 A * 9/1991 Guzman ..................... 204/452
5,858,187 A * 1/1999 Ramsey et al. .............. 204/452
6,001,229 A * 12/1999 Ramsey ....................... 204/451

OTHER PUBLICATIONS

Leshansky, A. M., et al., "Tunable Nonlinear Viscoelatic "Focusing" in a Microfluidic Device", Physical Review Letters, vol. 98, Jun. 8, 2007, p. 234501-1 to 234501-4.*

Bransky, A., et al., "An automated cell analysis sensing system based on a microfabricated rheoscope for the study of red blood cells physiology", Biosensors and Bioelectronics, vol. 22, 2006, p. 165-169.*
Repetti, R. V., and E. F. Leonard, "Segre-Silberberg annulus formation: a possible explanation", Nature, vol. 203, Sep. 26, 1964, p. 1346-1348.*
Stephen C. Jacobson and J. Michael Ramsey, "Electrokinetic Focusing in Microfabricated Channel Structures", Analytical Chemistry, vol. 69, No. 16, Aug. 15, 1997, 3212-3217, Oak Ridge National Laboratory, P.O. Box 2008, Oak Ridge, TN 37831-6142.
Stephen C. Jacobson and J. Michael Ramsey, "2D focusing", Electrokinetic Focusing in Microfabricated Channel Structures, Anal. Chem. 1997, 69, Oak Ridge National Laboratory, P.O. Box 2008, Oak Ridge, TN 37831-6142, 1 page.
Young Won Kim & Jung Yul Yoo, "3D (Axisymmetric) focusing", Axisymmetric flow focusing of particles in a single microchannel, Received Sep. 2, 2008, Accepted Feb. 20, 2009, Published as an Advance Article on the web Mar. 5, 2009, DOI: 10.1039/b815286a. www.rsc.org/loc, 1 page.

* cited by examiner

Primary Examiner — J. Christopher Ball
(74) Attorney, Agent, or Firm — Daly, Crowley, Mofford & Durkee, LLP

(57) ABSTRACT

In a particle focusing apparatus and a method for focusing particles, the particle focusing apparatus includes a channel, a fixing member, a fluid feeding portion and a power supply. The channel has first and second ends and extends substantially in a line. The fixing member includes a first fixing portion connected to and fixing the first end, and a second fixing portion connected to and fixing the second end. The fluid feeding portion feeds fluid having particles into the channel. The power supply has first and second terminals. The first terminal passes through the first fixing portion and is electrically connected to an anode of the power supply. The second terminal passes through the second fixing portion and is electrically connected to a cathode of the power supply. Thus, particles fed into the channel may be more easily and efficiently focused to a central region inside the channel.

7 Claims, 7 Drawing Sheets

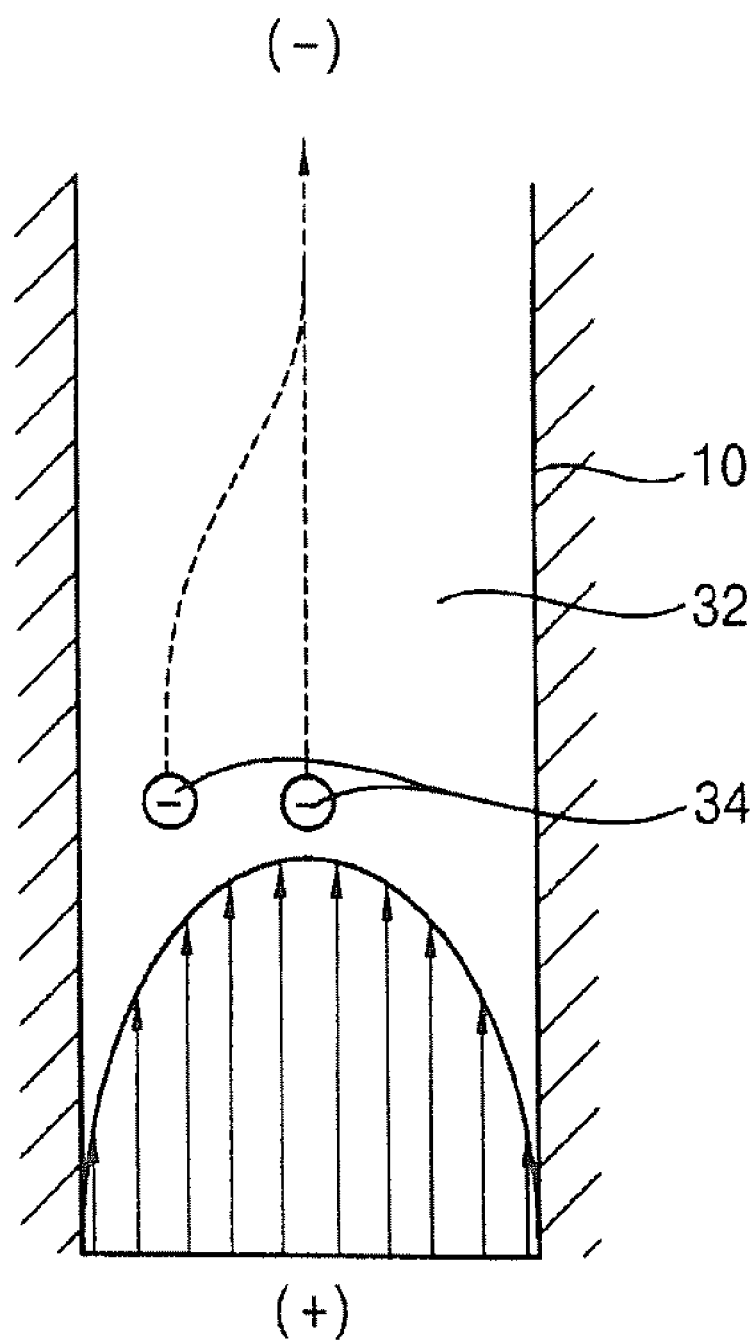

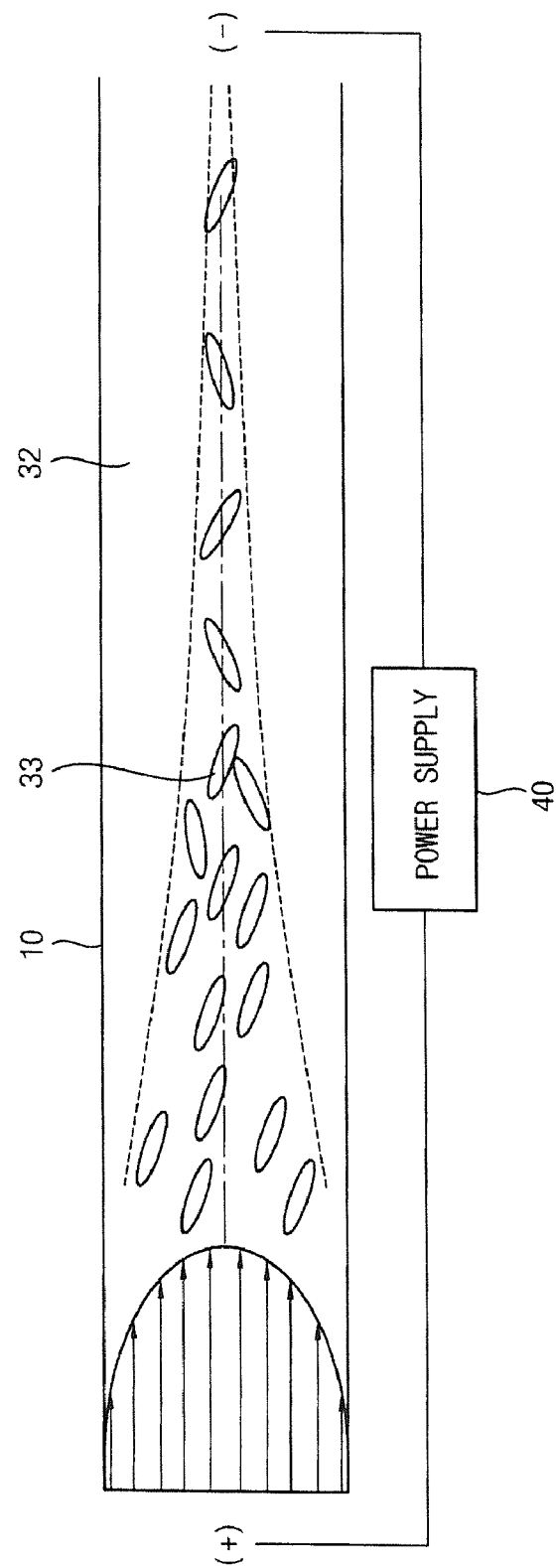

PARTICLE FOCUSING APPARATUS AND METHOD FOR FOCUSING PARTICLES BY USING THE SAME

CROSS-REFERENCE TO RELATED APPLICATIONS

This application claims priority under 35 U.S.C. §119 to Korean Patent Application No. 2007-80822, filed on Aug. 10, 2007 in the Korean Intellectual Property Office (KIPO), the contents of which are herein incorporated by reference in their entirety.

BACKGROUND OF THE INVENTION

1. Field of the Invention

The present invention relates to a particle focusing apparatus and a method for focusing particles. More particularly, the present invention relates to a particle focusing apparatus capable of enhancing focusing and a method for focusing particles by using the particle focusing apparatus.

2. Description of the Related Art

Flow cytometers have been widely used for cell sorting and counting in the field of medical diagnosis. Typically, cells or particles are injected into the capillary and hydrodynamically focused into a cell or particle stream constrained by two planar sheath flows or a concentric sheath flow. Then, this stream is passed through a sensing region for cell or particle counting or sorting. One of the key techniques of the flow cytometer is to focus the cells or the particles in a narrow region, where the cells or the particles may be highly concentrated. Nowadays, as micro-fluidic technology and microelectromechanical systems (MEMS) technology are being developed, research is being conducted on a flow cytometer that can be miniaturized into lab-on-a-chip system.

Generally, it is reported that the hydrodynamic focusing of particulate materials in microchannels is achieved two-dimensionally by using sheath flows. However, in a conventional flow cytometer, the focusing should be performed three-dimensionally for the best performance. Therefore, nowadays, research is being conducted on fabricating microchannels on a lab-on-a-chip device for three-dimensional hydrodynamic focusing based on the sheath flow technique using three-dimensional channel geometry. In this case, complicated microchannels are inevitable, resulting in high manufacturing costs and low productivity. The objective of the present invention is to provide axisymmetric or three-dimensional focusing of the particles in a single straight channel without sheath flows.

SUMMARY OF THE INVENTION

The present invention provides a particle focusing apparatus capable of enhancing particle focusing.

The present invention also provides a method for focusing particles by using the particle focusing apparatus.

In an example particle focusing apparatus according to the present invention, the particle focusing apparatus includes a channel, a fixing member, a fluid feeding portion, and a power supply. The channel has first and second ends, and extends substantially in a line. The fixing member includes a first fixing portion that is connected to the first end and fixes the first end, and a second fixing portion that is connected to the second end and fixes the second end. The fluid feeding portion passes through the first fixing portion to be connected to the first end, and feeds fluid having particles into the channel at a predetermined pressure. The power supply has first and second terminals. The first terminal passes through the first fixing portion to be connected to the first end and is electrically connected to an anode of the power supply. The second terminal passes through the second fixing portion to be connected to the second end and is electrically connected to a cathode of the power supply.

The fluid may include distilled water or distilled water having an electrolyte, and the particles inside the fluid may be negatively (−) charged.

An inner diameter of the channel may be between about 5 times and about 70 times larger than a particle diameter.

In another example particle focusing apparatus according to the present invention, the particle focusing apparatus includes a channel, a fixing member, a fluid feeding portion and a power supply. The channel has first and second ends, and extends substantially in a line. The fixing member includes a first fixing portion that is connected to the first end and fixes the first end, and a second fixing portion that is connected to the second end and fixes the second end. The fluid feeding portion passes through the first fixing portion to be connected to the first end, and feeds fluid having particles into the channel at a predetermined pressure. The power supply has first and second terminals. The first terminal passes through the first fixing portion to be connected to the first end and is electrically connected to a cathode of the power supply. The second terminal passes through the second fixing portion to be connected to the second end and is electrically connected to an anode of the power supply.

The fluid may include distilled water or distilled water having an electrolyte, and the particles inside the fluid may be positively (+) charged.

In an example method for focusing particles by using a particle focusing apparatus according to the present invention, the method includes forming a channel having first and second ends and extending substantially in a line. The first and second ends of the channel are respectively formed via connecting a first fixing portion of a fixing member to the first end of the channel and connecting a second fixing portion of the fixing member to the second end of the channel. Fluid having particles is fed into the channel at a predetermined pressure, through a fluid feeding portion passing through the first fixing portion to be connected to the first end. A voltage difference between first and second terminals of a power supply is generated via connecting the first terminal of the power supply to an anode of the power supply and connecting the second terminal of the power supply to a cathode of the power supply. The first terminal passes through the first fixing portion to be connected to the first end. The second terminal passes through the second fixing portion to be connected to the second end.

The fluid may include distilled water or distilled water having an electrolyte, and the particles inside the fluid may be negatively (−) charged.

The channel may be formed by forming an inner diameter of the channel to be between about 5 times and about 70 times larger than a particle diameter.

The fluid may be fed into the channel by maintaining a velocity of the fluid feeding into the channel to be a parabolic distribution, so that the velocity of the fluid may be maximum at a central region inside the channel and the velocity of the fluid may be decreased in a direction from the central region toward a side wall of the channel. The particles may be focused inside the fluid to the central region inside the channel.

In another example method for focusing particles by using a particle focusing apparatus according to the present invention, the method includes forming a channel having first and second ends and extending substantially in a line. The first and second ends of the channel are respectively fixed, via connecting a first fixing portion of a fixing member to the first end of the channel and connecting a second fixing portion of the fixing member to the second end of the channel. Fluid having particles is fed into the channel at a predetermined pressure, through a fluid feeding portion passing through the first fixing portion to be connected to the first end. A voltage difference between first and second terminals of a power supply may be generated via connecting the first terminal of the power supply to a cathode of the power supply and connecting the second terminal of the power supply to an anode of the power supply. The first terminal passes through the first fixing portion to be connected to the first end. The second terminal passes through the second fixing portion to be connected to the second end.

The fluid may include distilled water or distilled water having an electrolyte, and the particles inside the fluid may be positively (+) charged.

According to the present invention, the fluid having the particles is fed into the channel at the predetermined pressure and the voltage is applied to the channel, so that the focusing of the particles to the central region inside the channel may be enhanced.

In addition, the particles are focused along a central axis of the channel, so that the particles may be more easily detected and extracted.

In addition, the particles are focused without forming the channel complicatedly, so that manufacturing costs for the particle focusing apparatus may be decreased. Thus, productivity for the particle focusing apparatus may be enhanced.

BRIEF DESCRIPTION OF THE DRAWINGS

The above and other features and advantages of the present invention will become more apparent by describing in detailed example embodiments thereof with reference to the accompanying drawings, in which:

FIGS. 2B and 2C are conceptual views illustrating a motion of the charged particles lagging behind a parabolic flow velocity profile when electric force is applied;

FIG. 3 is a conceptual view illustrating particles focused inside the channel in the particle focusing apparatus of FIG. 1.

DESCRIPTION OF THE EMBODIMENTS

Figure 1:
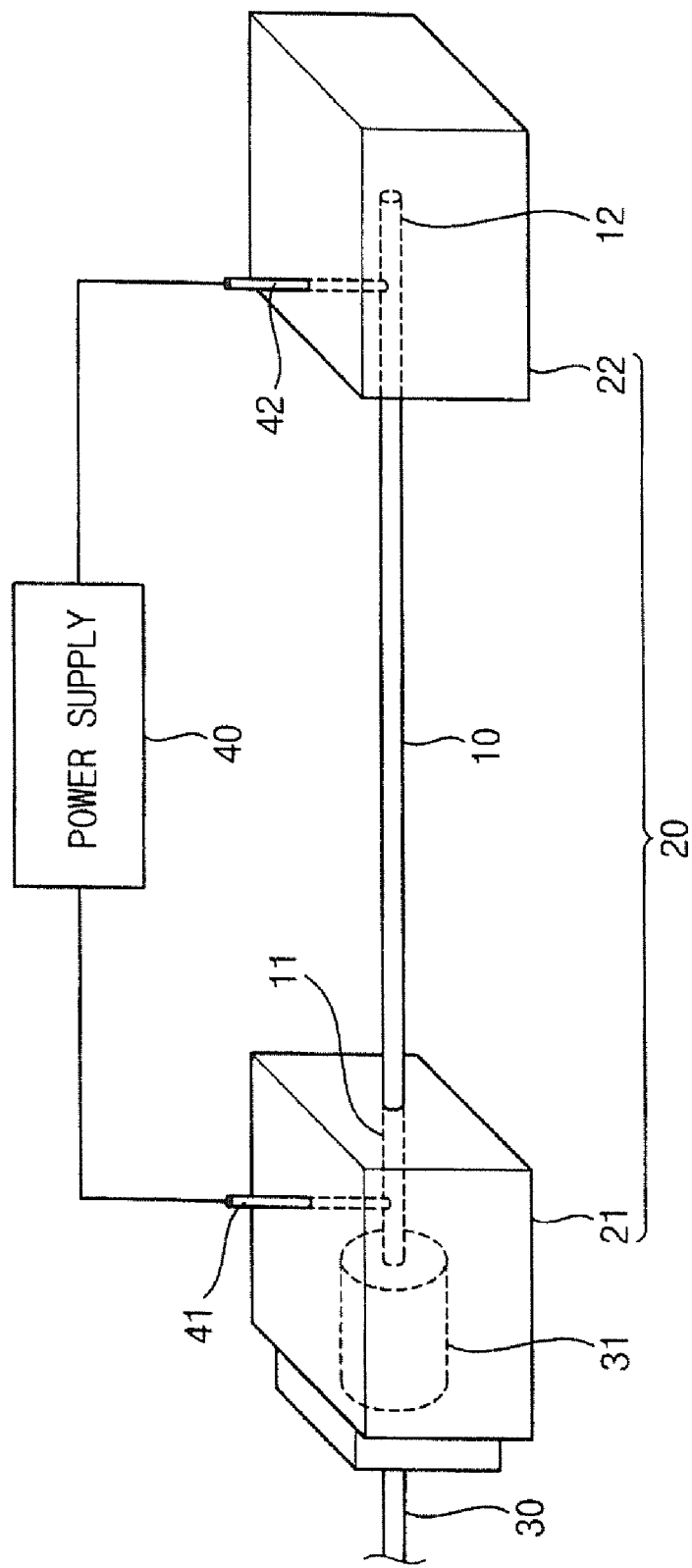
FIG. 1 is a conceptual view illustrating a particle focusing apparatus according to an example embodiment of the present invention.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that when an element or layer is referred to as being "on," "connected to" or "coupled to" another element or layer, it can be directly on, connected or coupled to the other element or layer, or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, the present invention will be explained in detail with reference to the accompanying drawings.

FIG. 1 is a conceptual view illustrating a particle focusing apparatus according to an example embodiment of the present invention.

Referring to FIG. 1, the particle focusing apparatus according to the present example embodiment includes a channel 10, a fixing member 20, a fluid feeding portion 30 and a power supply 40.

The channel 10 includes first and second ends 11 and 12, and extends substantially in a line. The first and second ends 11 and 12 are fixed by the fixing member 20, and are connected to the power supply 40. One of the first and second ends 11 and 12 is connected to the fluid feeding portion 30. For example, as illustrated in FIG. 1, the first end 11 is connected to the fluid feeding portion 30. Alternatively, the second end 12 may be connected to the fluid feeding portion 30. When the first end 11 is connected to the fluid feeding portion 30, the second end 12 may be connected to a fluid outlet portion (not shown), so that the fluid fed into the channel 10 may flow out. Alternatively, when the second end 12 is connected to the fluid feeding portion 30, the first end 11 may be connected to the fluid outlet portion (not shown).

The channel 10 has a cylindrical tunnel shape through which the fluid flows. A cross-sectional shape of the channel 10 may be a circular shape, and an inner diameter and a length of the channel 10 will be explained. Alternatively, the channel 10 may have a polygonal cylindrical tunnel shape, for example, a regular square cylindrical tunnel shape. In this case, the cross-sectional shape of the channel 10 may be a polygonal shape, for example, a regular square shape. In the present example embodiment, the channel 10 having the cylindrical tunnel shape will be explained, but the channel 10 having the polygonal cylindrical tunnel shape may be substantially the same as the channel 10 having the cylindrical tunnel shape. Accordingly, the cross-sectional shape of the channel 10 is the circular shape or the polygonal shape, so that the channel 10 according to the present example embodiment may be of wide application. In particular, the present example embodiment may be applied to lab-on-a-chip apparatuses when a cross-sectional shape of the channel 10 includes a square shape.

For example, the channel 10 includes a non-conductive material. Thus, when the power supply 40 applies a voltage to the first and second ends 11 and 12, an electrical potential between the first and second ends 11 and 12 may be generated. For example, the non-conductive material may be one of glass, a silicon-based resin, a polymer-based resin and an alloy resin thereof.

The fixing member 20 includes first and second fixing portions 21 and 22. For example, as illustrated in FIG. 1, the first and second fixing portions 21 and 22 have a hexahedron shape. The first and second fixing portions 21 and 22 are respectively connected to the first and second ends 11 and 12. Thus, the first fixing portion 21 fixes and covers the first end 11 of the channel 10, and the second fixing portion 22 fixes and covers the second end 12 of the channel 10. In addition, the first and second fixing portions 21 and 22 cover a connecting portion 31 between the fluid feeding portion 30 and the first end 11 or the second end 12, to prevent the fluid from leaking from the connecting portion 31. Alternatively, the first and second fixing portions 21 and 22 may have various shapes to fix and cover the first and second ends 11 and 12.

For example, the fixing member 20 includes the non-conductive material substantially the same as that of the channel 10.

The fluid feeding portion 30 passes through the first fixing portion 21 to be connected to the first end 11. In this case, the fluid outlet portion (not shown) may be connected to the second end 12, so that the fluid may flow out. Alternatively, although not shown in the figure, the fluid feeding portion 30 passes through the second fixing portion 21 to be connected to the second end 12, and the fluid outlet portion (not shown) may be connected to the first end 11.

The fluid is fed from the fluid feeding portion 30 into the channel 10 passing through the first end 11 at a predetermined pressure. The fluid fed into the channel 10 flows in the channel 10 at a predetermined velocity, and then flows out through the fluid outlet portion (not shown).

The fluid fed into the channel 10 through the fluid feeding portion 30 may include distilled water or distilled water having an electrolyte. In this case, an electrolyte solution containing the electrolyte contents dissolved in distilled water may be a sodium chloride aqueous solution where a small amount of sodium chloride (NaCl) is dissolved in the distilled water, a potassium chloride (KCl) aqueous solution where a small amount of potassium chloride is dissolved in the distilled water, the electrolyte content may be phosphate buffered saline (PBS), and so on.

The fluid may contain particles, and the particles may include cells, viruses, latex particles, high molecular weight polymers, nucleic acid, DNA and so on. For example, the fluid feeding portion 30 feeds the fluid having the particles such as the cells into the channel 10 at the predetermined pressure. Generally, most dielectric materials in nature, such as the particles mentioned above, have a negatively (−) charged surface in the electrolyte solution. Thus, the present invention may be of wide application to cell diagnosis apparatuses.

Both ends of the power supply 40 are respectively connected to first and second terminals 41 and 42. The first terminal 41 passes through the first fixing portion 21 to be connected to the first end 11, and the second terminal 42 passes through the second fixing portion 22 to be connected to the second end 12. For example, as illustrated in FIG. 1, the first and second terminals 41 and 42 are respectively connected to upper surfaces of the first and second fixing portions 21 and 22. Alternatively, the first and second terminals 41 and 42 may be connected to various positions of the first and second fixing portions 21 and 22.

The power supply 40 may generate the voltage difference between the first and second terminals 41 and 42. For example, as illustrated in FIG. 1, when the fluid feeding portion 30 is connected to the first end 11, the first terminal 41 is electrically connected to an anode (+) of the power supply 40, and the second terminal 42 is electrically connected to a cathode (−) of the power supply 40. Alternatively, although not shown in the figure, when the fluid feeding portion 30 is connected to the second end 12, the first terminal 41 is electrically connected to the cathode (−) of the power supply 40, and the second terminal 42 is electrically connected to the anode (+) of the power supply 40.

Figure 2A:
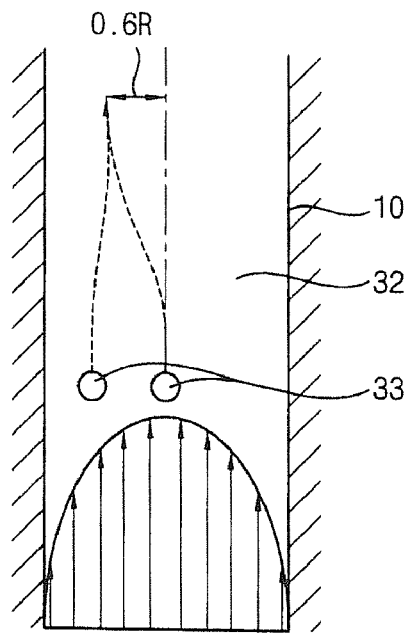
FIG. 2A is a conceptual view illustrating a motion of particles having a density substantially the same as that of fluid when no electric force is applied.

FIG. 2A is a conceptual view illustrating a motion of particles having a density substantially the same as that of a fluid when no electric force is applied.

Referring to FIG. 2A, when the predetermined pressure is applied to the fluid 32 fed into the channel 10 through the fluid feeding portion 30, a velocity profile according to the present example embodiment is parabolic in the channel 10. Generally, since the predetermined pressure is applied to the fluid 32 fed into the channel 10, the velocity profile of the fluid 32 is parabolic in the channel 10. When the velocity profile of the fluid 32 is parabolic and particles 33 are arbitrarily positioned in the fluid 32 of the channel 10, a motion of the particles 33 is affected by the velocity profile of the fluid 32 or a curvature of the velocity profile.

Generally, when the Reynolds number (Re) of the fluid 32 in the channel 10 is small, the particles in the channel 10 are uniformly distributed. However, according as the Reynolds number (Re) of the fluid 32 in the channel 10 increases, as illustrated in FIG. 2A, the particles in the channel 10 drift away from a side wall of the channel and from a central region inside the channel, and accumulate at a position 0.6R. In this case, R is a radius of the channel 10.

Figure 2B:
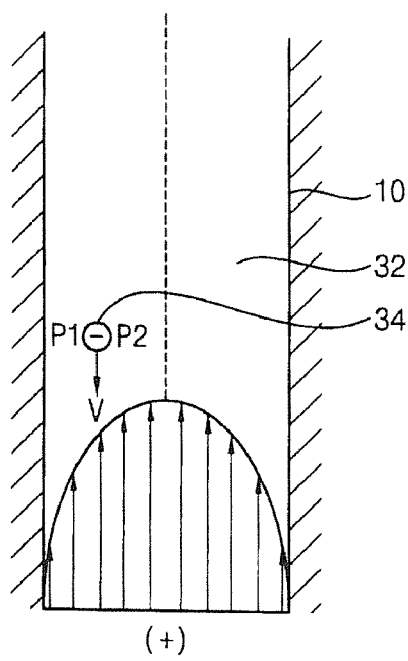

FIGS. 2B and 2C are conceptual views illustrating a motion of the charged particles lagging behind a parabolic flow velocity profile when electric force is applied.

Referring to FIGS. 2B and 2C, the charged particle 34 has a tendency to move against the direction of the parabolic fluid flow because the direction of the electrophoretic mobility of the particle 34 is opposite to that of the predetermined velocity V(r). Thus, apparent velocity of the charged particle 34 has a lower velocity than the predetermined velocity V(r) at a certain radial position. For example, the charged particle 34 lags behind the predetermined velocity V(r). In this case, a pressure difference between a first pressure P1 and a second pressure P2 occurs. The first pressure P1 is a pressure in a first area between the particle 34 and the side wall of the channel 10, and the second pressure P2 is a pressure in a second area between the particle 34 and the central region inside the channel 10. When the particle 34 lags behind the fluid, the first pressure P1 is less than the second pressure P2. Accordingly, when the first pressure P1 becomes larger than the second pressure P2, the charged particle 34 moves near the central region of the channel 10, and thus the charged particle 34 is focused near the central region of the channel 10. The present example embodiment may be applied to all cases including the case when the charged particle 34 lags behind the predetermined velocity profile (parabolic velocity profile) by using an opposite electrophoretic mobility of the particle against the predetermined velocity profile.

FIG. 3 is a conceptual view illustrating particles focused inside the channel in the particle focusing apparatus of FIG. 1.

Referring to FIG. 3, the first end 11 of the channel 10 is electrically connected to the anode (+) of the power supply 40, and the second end 12 of the channel 10 is electrically connected to the cathode (−) of the power supply 40. In addition, the velocity profile of the fluid 32 fed into the channel 10 is parabolic. In this case, the pressure is applied from the first end 11 that is electrically connected to the anode (+) of the power supply 40, to the second end 12 that is electrically connected to the cathode (−) of the power supply 40. Thus, the fluid 32 flows from the first end 11 to the second end 12 in the channel 10.

Alternatively, the first end 11 may be electrically connected to the cathode (−) of the power supply 40, and the second end 12 may be electrically connected to the anode (+) of the power supply 40. In this case, the power may be applied from the second end 12 to the first end 11. Thus, the fluid 32 flows from the second end 12 to the first end 11 in the channel 10.

Generally, when the voltage difference between both ends is generated, the charged particles suspended in the fluid 32 inside the channel move to an end that is charged with the opposite polarity to that of the charged particles. For example, when the particle is negatively (−) charged in the electrolyte solution, the particle migrates toward the positive electrode and vice versa. The movement of colloidal particles through a fluid under the influence of an electric field is known as electrophoresis. The electrophoresis causes a relative motion between the fluid and the particle. For example, when the electric field between both electrodes increases, the electrophoretic mobility of the particle increases, so that the movement of the charged particles is enhanced. Thus, the relative motion or slip motion between the fluid and the particle also increases, which enhances the particle focusing into the central region of the channel, when coupled with the parabolic velocity profile of the fluid inside the channel.

As explained referring to FIG. 2A, when the Reynolds number (Re) inside the channel 10 based on the predetermined pressure from the fluid feeding portion is small, the particles in the channel 10 are uniformly distributed across the channel. However, when the particles in the channel 10 are negatively (−) charged and the electric field is applied between two electrodes by using the power supply 40, the electric force may be exerted on each of the particles due to the electrophoretic mobility. In the present example embodiment, the direction of the particle movement due to the electrophoretic mobility along the central region of the channel is opposite to that of the parabolic velocity profile due to the predetermined pressure. For example, considering that the particle is negatively (−) charged, when the cathode (−) of the power supply 40 is connected to the second end and the anode (+) of the power supply 40 is connected to the first end 11, the fluid 32 with the parabolic velocity profile may be fed from the first end to the second end, where the particle lags behind fluid flows.

If the direction of electrophoretic mobility of the particle is opposite to that of the parabolic velocity profile of the fluid, where the particle is negatively charged and the fluid 32 is fed from the first end to the second end, under the condition that the cathode (−) of the power supply 40 is connected to the first end and the anode (+) of the power supply is connected to the second end, the particle lags behind the fluid 32 with the parabolic velocity profile. Thus, in this case, as illustrated in FIG. 2B, the first pressure P1 is less than the second pressure P2 due to the relative motion. Thus, the charged particle 34 moves toward the central region inside the channel 10, and thus the charged particle 34 is focused near the central region inside the channel 10. The focusing of the particles may be more enhanced, as the resident time of the particle in the channel is longer. For example, the particles are focused into a narrower region near the central region inside the channel, as the particles travel closer to the second end 12 that is electrically connected to the cathode (−) of the power supply 40. Thus, outermost edges of the particle beam are indicated with dotted lines in FIG. 3.

For example, the inner diameter of the channel 10 may be between 5 times and 70 times larger than the particle diameter, so that the particles may be focused near the central axis of the channel 10. When the inner diameter of the channel 10 is lower than 5 times the particle diameter, the focusing of the particles may be meaningless. In addition, when the inner diameter of the channel 10 is larger than 70 times the particle diameter, the particles may be less focused, so that the particles are difficult to inspect or extract.

As mentioned above, the particles in the channel 10 may be positively (+) charged. In this case, although not shown in the figure, the first end 11 of the channel 10 is electrically connected to the cathode (−) of the power supply 40, and the second end 12 of the channel 10 is electrically connected to the anode (+) of the power supply 40. In addition, the velocity profile of the fluid 32 in the channel 10 is parabolic due to the predetermined pressure. In this case, the pressure is applied from the first end 11 that is electrically connected to the cathode (−) of the power supply 40 to the second end 12 that is electrically connected to the anode (+) of the power supply 40. For example, the fluid 32 flows from the first end 11 to the second end 12 in the channel 10.

Alternatively, when the particles in the channel 10 are positively (+) charged, the first end 11 may be electrically connected to the anode (+) of the power supply 40 and the second end 12 may be electrically connected to the cathode (−) of the power supply 40. In this case, the pressure is applied from the second end 12 that is electrically connected to the cathode (−) of the power supply 40 to the first end 11 that is electrically connected to the anode (+) of the power supply 40. For example, the fluid 32 flows from the second end 12 to the first end 11 in the channel 10.

Accordingly, when the particles in the channel 10 are negatively (−) charged, the pressure is preferably applied from the anode (+) of the power supply 40 to the cathode (−) of the power supply 40. In addition, when the particles in the channel 10 are positively (+) charged, the pressure is preferably applied from the cathode (−) of the power supply 40 to the anode (+) of the power supply 40, so that the particle focusing apparatus according to the present example embodiment may cause the particle to lag behind the fluid 32 with the parabolic velocity profile. Thus, the particles may be focused due to the pressure difference between the first pressure P1 and the second pressure P2 near the central region inside the channel 10, which is induced by electrophoretic particle motion against the fluid flow with the parabolic velocity profile.

FIGS. 4A to 4F are graphs illustrating the particles focused according to a voltage per unit length of the channel. FIGS. 4A to 4F illustrates concentration profiles of the particle according to a voltage per unit length (V/cm), and experimental conditions are given in Table 1. In FIGS. 4A to 4F, an x-axis shows a normalized radial position of the channel and a y-axis shows a particle concentration presented as a probability density function (F(r)). The present example embodiment includes the particles which are negatively (−) charged. The experimental results according to the present example embodiment may be substantially applied to the particles which are positively (+) charged.

Referring to Table 1, a volume flow rate of the fluid used in the present example embodiment was about 20 μL/h. The fluid was fed into the channel 10 with the pressure that caused the parabolic velocity profile with a maximum fluid velocity of about 1.7 mm/s at the central region inside the channel 10. As a working fluid, a 22% water-glycerol mixture was used for the experiment. The inner diameter of the channel 10 was about 87 μm. The channel 10 includes the non-conductive material. For example, the channel 10 may include fluorinated ethylene polymer (FEP) that is a kind of Teflon.

TABLE 1

| Flow Characteristics | Unit flux: 20 μL/h [maximum velocity: 1.7 mm/s] Fluid: 22% distilled water-glycerol mixture Inner diameter of channel: 87 μm |
|---|---|
| Particle Characteristics | Particle diameter: 5 μm Surface polarity of particles: negative (−) charge Volume fraction of particles in fluid: 0.005% |
| Voltage per Unit Length [V/cm] | 0   42.8   64.3   85.7   107.1   128.6 |

The particle diameter was about 5 μm. Thus, as mentioned above, the inner diameter of the channel 10 was about 17 times larger than the particle diameter, so that the inner diameter of the channel 10 is between about 5 times and 70 times the particle diameter. The particles were negatively (−) charged in the distilled water-glycerol mixed solution, and a volume fraction of the particles in the fluid was about 0.005%.

In addition, as the applied voltage between the first and second terminals 41 and 42 increases as shown in Table 1, the evolution of the focusing of the particles was measured.

Figure 4A:
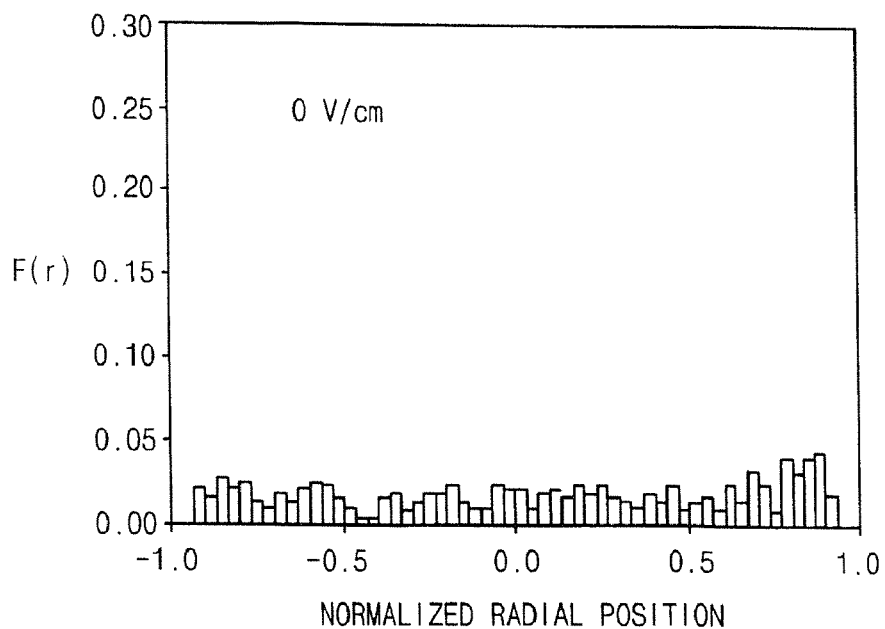
FIGS. 4A to 4F are graphs illustrating the particles focused according to a voltage per unit length of the channel.

Referring to FIG. 4A, when the voltage difference per unit length is about 0 V/cm, the particles are uniformly distributed in the channel 10. As mentioned above, when the velocity of the fluid is parabolically distributed in the channel 10 and the Reynolds number (Re) of the fluid is small, the particles are uniformly distributed over the cross-section of the channel 10.

Figure 4B:
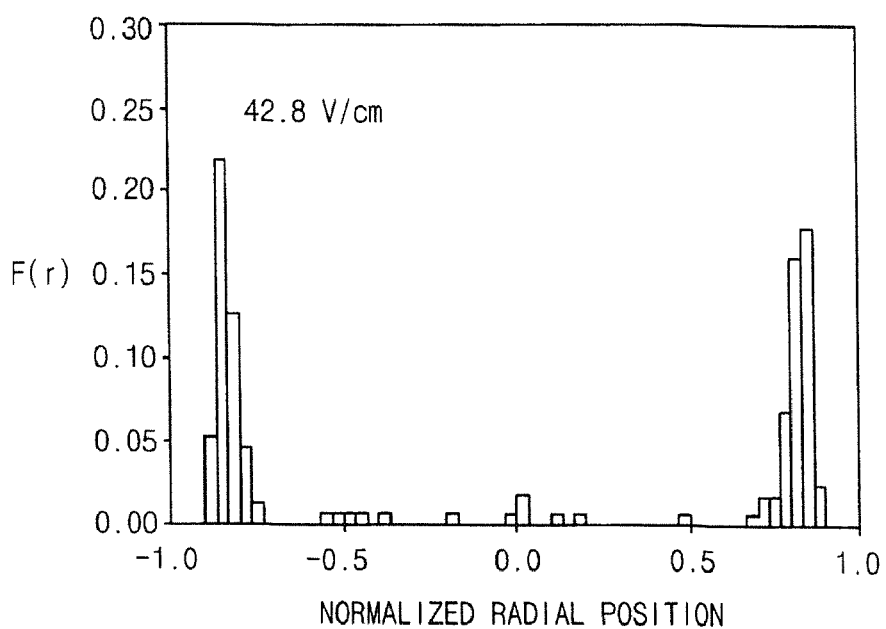
Figure 4C:
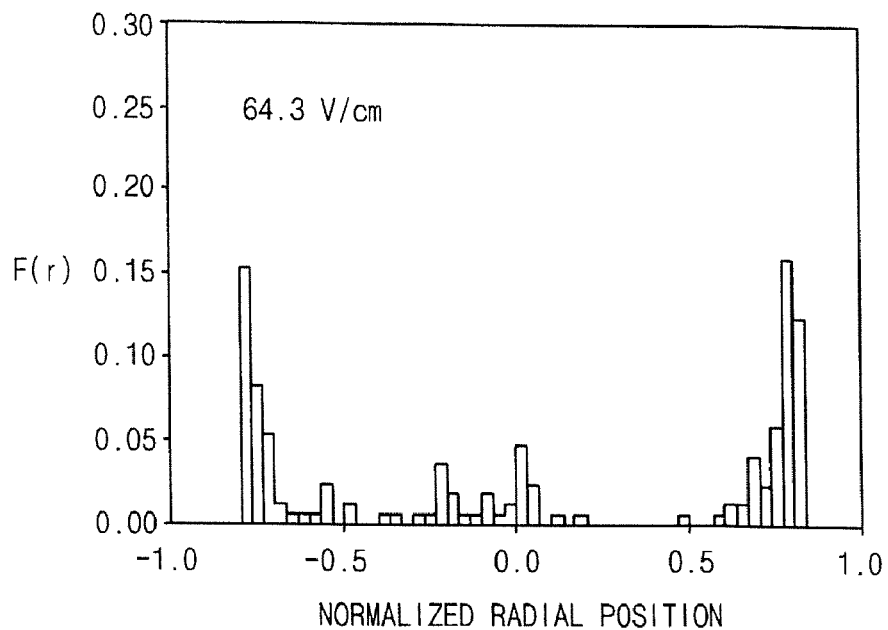

Referring to FIGS. 4B and 4C, when the voltage difference per unit length increases from about 42.8 V/cm to about 64.3 V/cm, the particles have a tendency to be focused near the side wall of the channel 10. For example, when the voltage difference is low, the electrophoretic mobility of the particles is low, so that a small lagging motion exists between the fluid and the particle. In this case, the particle moves toward the side wall of the channel. Thus, the particles are spaced apart from the central region inside the channel 10.

Figure 4D:
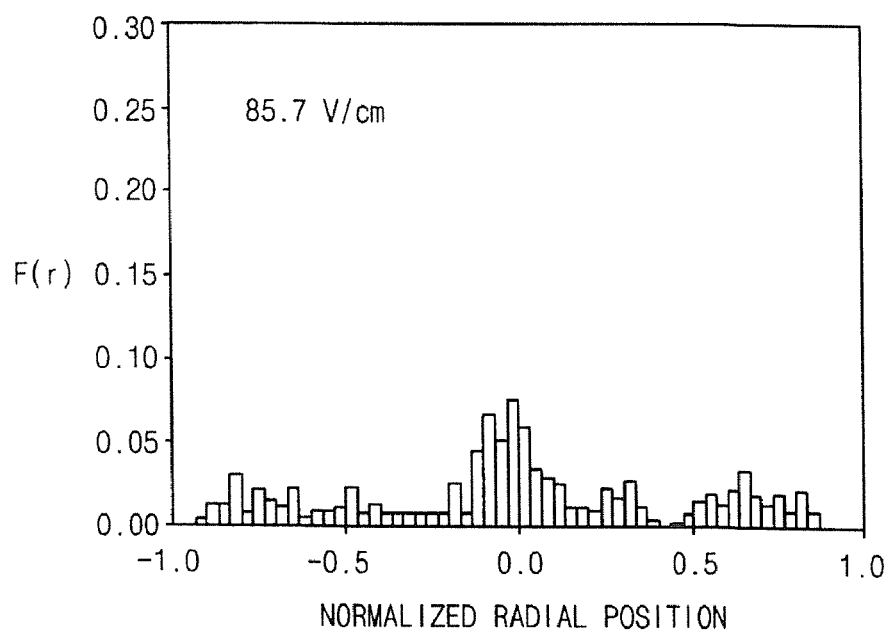
Figure 4E:
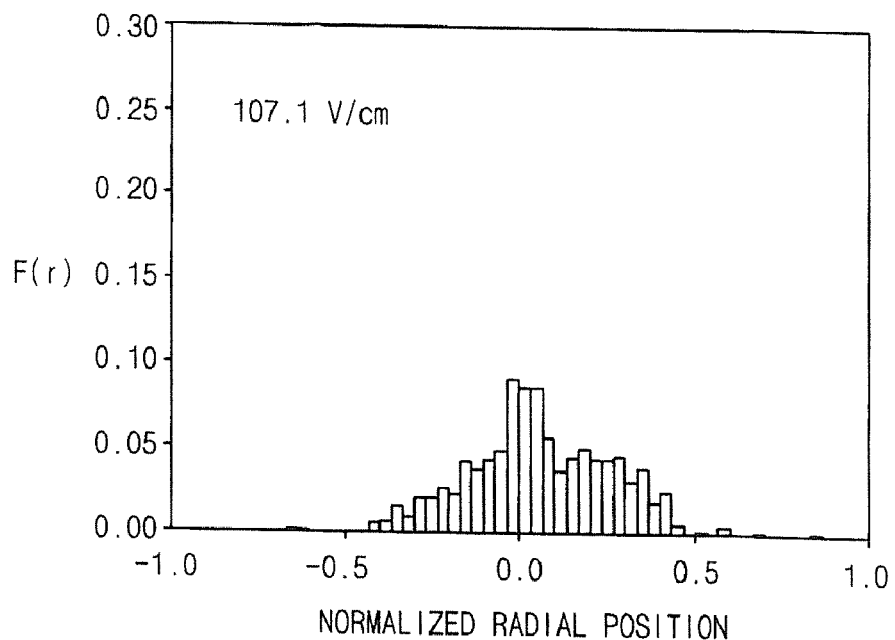

Referring to FIGS. 4D and 4E, as the voltage difference per unit length increases from about 85.7 V/cm to about 107.1 V/cm, the number of the particles that are focused near the central region inside the channel 10 increases. For example, as the voltage difference per unit length increases, the electrophoretic mobility of the particles increases, so that a large lagging motion exists between the fluid and the particle. Thus, the number of the particles focused near the central region inside the channel 10 increases.

Figure 4F:
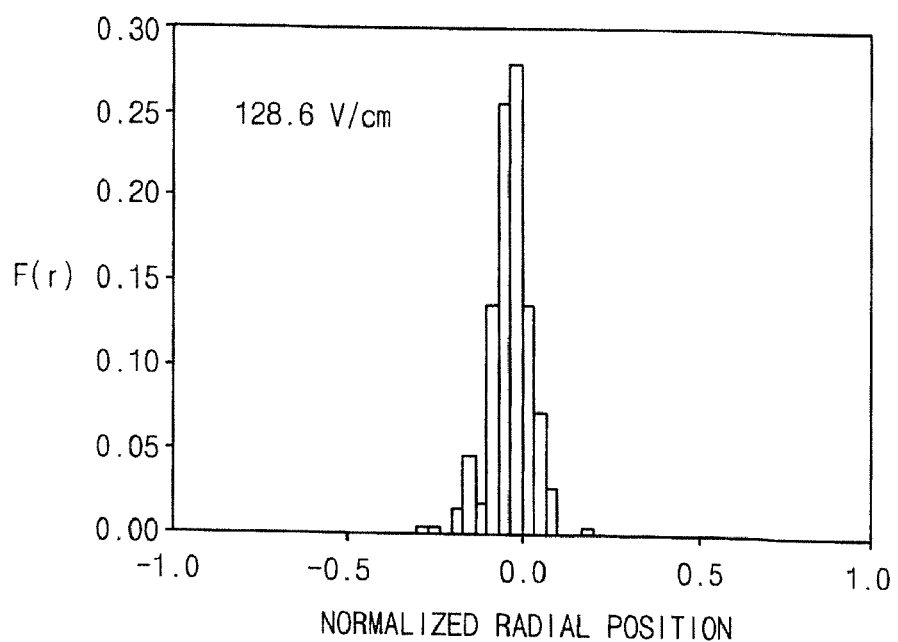

Referring to FIG. 4F, when the voltage difference per unit length is maintained at about 128.6 V/cm, the number of the particles focused near the central region inside the channel 10 remarkably increases, which gives higher efficiency for detecting the particles or the cells in a flow cytometer.

For example, when the length of the channel is about 7 cm and the voltage difference between the first and second terminals 41 and 42 is about 900 V, the voltage difference per unit length may be maintained about 128.6 V/cm.

FIGS. 4A to 4F are the experimental results carried out under the experimental conditions in Table 1, and the particle focusing apparatus and the method for focusing the particles according to the present invention may be embodied with various experimental conditions and should not be construed as limited to the experimental conditions shown in Table 1.

According to the present invention, a fluid having particles is fed into a channel at a predetermined pressure and a voltage is applied to the channel, so that the focusing of the particles to a central region inside the channel may be enhanced.

In addition, the particles are focused along a central axis of the channel, so that the particles may be more easily detected and extracted.

In addition, the particles are axisymmetrically focused in a single straight channel without forming the channel complicatedly, so that manufacturing costs for the particle focusing apparatus may be decreased. Thus, productivity for the particle focusing apparatus may be enhanced.

What is claimed is:

1. A method for focusing particles by using a three-dimensional particle focusing apparatus, the method comprising:

forming a single sufficiently-extended straight channel having first and second ends, the channel not having an intersection with a branch channel;

fixing the first and second ends of the channel respectively, via connecting a first fixing portion of a fixing member to the first end of the channel and connecting a second fixing portion of the fixing member to the second end of the channel, the first fixing portion and the second fixing portion being separately formed from each other and being spatially isolated from each other;

feeding fluid having particles into the channel at a predetermined pressure, through a fluid feeding portion passing through the first fixing portion to be connected to the first end of the channel; and generating a voltage difference between first and second terminals of a power supply, via connecting the first terminal of the power supply to a positive electrode of the power supply and connecting the second terminal of the power supply to a negative electrode of the power supply, the first terminal passing through the first fixing portion to be connected to the first end of the channel, the second terminal passing through the second fixing portion to be connected to the second end of the channel, wherein the channel has a cross section of a circle, wherein the three-dimensional particle focusing apparatus focuses the particles along a central point of the circle of the channel without sheath flows, and wherein the channel is only supported by the first fixing portion and the second fixing portion at the first and second ends of the channel.

2. The method of claim 1, wherein the fluid includes distilled water or distilled water having an electrolyte, and the particles inside the fluid are negatively (−) charged.

3. The method of claim 1, wherein the channel is formed by forming an inner diameter of the channel to be between about 5 times and about 70 times larger than a particle diameter.

4. The method of claim 1, wherein the fluid is fed into the channel by maintaining a velocity of the fluid fed into the channel to be a parabolic distribution, so that the velocity of the fluid is maximum at a central region inside the channel and the velocity of the fluid decreases along a radial direction from the center to a side wall in the channel.

5. The method of claim 4, further comprising focusing the particles in the fluid to the center in the channel.

6. A method for focusing particles by using a three-dimensional particle focusing apparatus, the method comprising:

forming a single sufficiently-extended straight channel having first and second ends, the channel not having an intersection with a branch channel;

fixing the first and second ends of the channel respectively, via connecting a first fixing portion of a fixing member to the first end of the channel and connecting a second fixing portion of the fixing member to the second end of the channel, the first fixing portion and the second fixing portion being separately formed from each other and being spatially isolated from each other;

feeding fluid having particles into the channel at a predetermined pressure, through a fluid feeding portion passing through the first fixing portion to be connected to the first end of the channel; and generating a voltage difference between first and second terminals of a power supply, via connecting the first terminal of the power supply to a negative electrode of the power supply and connecting the second terminal of the power supply to a positive electrode of the power supply, the first terminal passing through the first fixing portion to be connected to the first end of the channel, the second terminal passing through the second fixing portion to be connected to the second end of the channel, wherein the channel has a cross section of a circle, wherein the three-dimensional particle focusing apparatus focuses the particles along a central point of the circle of the channel without sheath flows, and wherein the channel is only supported by the first fixing portion and the second fixing portion at the first and second ends of the channel.

7. The method of claim 6, wherein the fluid includes distilled water or distilled water having an electrolyte, and the particles inside the fluid are positively (+) charged.

* * * * *